(12) United States Patent
Castillo et al.

(10) Patent No.: US 7,955,711 B2
(45) Date of Patent: Jun. 7, 2011

(54) WOOD TREATMENT SOLUTION AND PROCESS

(75) Inventors: Donald Castillo, Garden City Beach, SC (US); Charles K. Elliott, Jr., Greenville, SC (US); Christopher Patton Bennett, Roebuck, SC (US)

(73) Assignee: Preventive Technology, Inc., Greenville, SC (US)

( * ) Notice: Subject to any disclaimer, the term of this patent is extended or adjusted under 35 U.S.C. 154(b) by 294 days.

(21) Appl. No.: 11/986,162

(22) Filed: Nov. 20, 2007

(65) Prior Publication Data

US 2009/0130475 A1     May 21, 2009

(51) Int. Cl.
*B27K 3/20*     (2006.01)

(52) U.S. Cl. ............... 428/532; 428/536; 428/537.1; 428/402; 427/397.7; 162/24

(58) Field of Classification Search .............. 428/536, 428/537.1, 402, 532; 427/397.1; 162/24
See application file for complete search history.

(56) References Cited

U.S. PATENT DOCUMENTS

| | | | | |
|---|---|---|---|---|
| 3,306,765 | A * | 2/1967 | Du Fresne et al. | 428/541 |
| 5,478,598 | A | 12/1995 | Shiozawa | 427/297 |
| 6,528,175 | B2 * | 3/2003 | Grantham et al. | 428/541 |
| 6,770,168 | B1 * | 8/2004 | Stigsson | 162/24 |
| 6,827,984 | B2 * | 12/2004 | Slimak et al. | 427/397.7 |

* cited by examiner

*Primary Examiner* — Leszek Kiliman
(74) *Attorney, Agent, or Firm* — Thomas L. Moses; Monahan & Moses, LLC

(57) ABSTRACT

The present invention features a single aqueous solution that imparts acceptable levels of water resistance, fire resistance, mold resistance and pest resistance to wood, and which may be used in standard wood treatment techniques commonly utilized in the wood treatment industry. The aqueous solution contains a fire retardant, an insect and termite repellant, a mold inhibitor and a pH buffer.

27 Claims, No Drawings

WOOD TREATMENT SOLUTION AND PROCESS

BACKGROUND OF THE INVENTION

The present invention is directed to a treatment for wood and wood products that is water resistant, fire resistant, and includes a mold and pest inhibitor. More specifically, the present invention is a solution (and a powder mixture that may be used to form a solution) that may be applied to wood and wood products using pressure treatment techniques that are currently used in the wood treatment industry.

Typically, a treatment method includes the steps of placing the wood product into a pressure vessel and applying a vacuum, contacting the material with an aqueous solution and increasing the pressure in the pressure vessel, draining the aqueous solution and reducing the pressure, and drying the treated wood product. Heretofore, efforts have been made to treat wood in order to achieve various results, including water resistance, mold inhibition, pest (specifically termite) inhibition, and further including a fire retardant. Many different chemicals have been used for these purposes, including silicates, chromium compounds, arsenic based compounds, copper and zinc based formulations, creosote, copper naphthenate, pentachlorophenol and chromate copper arsenate.

U.S. Pat. No. 3,306,765 describes a method for fireproofing wood, which includes the use of an alkali silicate solution together with a borate to impart fire resistant properties to wood, but includes the expensive and environmentally unpopular second step of exposing the treated wood to carbon dioxide at a pressure of about 300 to about 800 p.s.i. to produce polymerization of the silicate/borate combination within the wood. One drawback to this method is that carbon dioxide is considered a greenhouse gas, and releasing large amounts of it in the treatment process could be considered environmentally harmful.

U.S. Pat. No. 6,827,984 is directed to a process of using sodium silicate to create fire retardant products by immersing wood products in a soluble silicate solution, and then drying the wood at elevated temperatures, between 150° C. and 650° C. to cause the silicate solution to become insoluble within the wood.

The use of many of the solutions used for treating wood in the past have certain drawbacks, including the expense of the component products or processes required (including energy usage), the environmental hazards posed, and the safety considerations associated with human contact with such formulations. Further, to date, it has not been possible to provide a single aqueous solution that may be used in standard or pre-existing wood treatment processes that provides a combination of water repellence, fire resistance, mold resistance and pest or termite resistance.

Therefore, it would be desirable to provide a single aqueous wood treatment solution that imparts these characteristics in wood and wood products without using heavy metal compounds, is less expensive to manufacture than existing products, uses lower drying temperatures (and therefore less energy), poses less human safety hazards, and is more environmentally friendly than such existing products and processes.

SUMMARY OF THE INVENTION

The object of the present invention is to overcome the aforementioned limitations and shortcomings of the prior art. The present invention features a single aqueous solution that imparts acceptable levels of water resistance, fire resistance, mold resistance and pest resistance to wood, and which may be used in standard wood treatment techniques commonly utilized in the wood treatment industry. The proposed aqueous solution is less expensive to manufacture than solutions currently available, and may be used in a single batch process to impart the four aforementioned desired qualities.

In one preferred embodiment, the aqueous solution comprises a fire retardant, preferably sodium metasilicate nonahydrate (about 5% to 30% by mass), an insect and termite repellant, preferably sodium tetraborate decahydrate—also known as borax—(about 1.5% to 9% by mass), a mold inhibitor, preferably thymol (about 0.01% to 0.1% by mass) or ethanolamine (about 0.5% to 20% by mass), and a pH buffer, preferably sodium carbonate (about 1% to 10% by mass). It is believed that the borate/silicate components polymerize upon drying, and become water insoluble, which in turn prevents leaching and provides water repellent characteristics to the wood after treatment. It has been observed that the sodium carbonate may also act as a mold inhibitor, so that the ethanolamine and thymol may be optional ingredients in the solution. The sodium carbonate, in addition to serving as a buffer and imparting some mold and mildew inhibiting properties, is thought to also serve as a catalyst that maintains the water solubility before and during the immersion (impregnation) step, and helps to polymerize the silicate/borate compounds during the drying step. The aqueous solution should have a pH in the range of 9.5 and 13.

One problem associated with using borates and silicates in solution is that under many conditions, the presence of one compound tends to make the other polymerize and precipitate out of solution. In order to maintain water solubility of the aqueous solution containing the borates and silicates, it is important to maintain the proper pH (which in this case is maintained by the sodium carbonate component), and further to add the borate and silicate compounds to the solution in the proper sequence and within the proper mass percentage ranges.

DETAILED DESCRIPTION OF THE INVENTION

Without limiting the scope of the invention, the preferred embodiments and features are hereinafter set forth. The present invention is directed to an aqueous solution that may be applied to wood and wood products using standard pressure treatment techniques, wherein the solution will impart the following qualities to the wood products: fire retardance, water resistance, mold inhibition and termite resistance.

In one preferred embodiment, the aqueous solution comprises a fire retardant, preferably sodium metasilicate nonahydrate (about 5% to 30% by mass), an insect and termite repellant, preferably sodium tetraborate decahydrate—also known as borax—(about 1.5% to 9% by mass), a mold inhibitor, preferably thymol (about 0.01% to 0.1% by mass) or ethanolamine (about 0.5% to 20% by mass), and a pH buffer, preferably sodium carbonate (about 1% to 10% by mass). It is believed that the silicate polymerizes together with the borate when dried in order to prevent leaching. It has been observed that the sodium carbonate may also act as a mold and mildew inhibitor, so that the ethanolamine and thymol may be optional ingredients in the solution.

It should be understood that other compounds may be used for the various components. For instance, another acceptable silicate is potassium metasilicate, which may be used in the same concentration range as the sodium metasilicate nonahydrate. Also, sodium orthosilicate may be used as an acceptable silicate, in the same concentration range as the sodium metasilicate nonahydrate. Other soluble borates may be used, including disodium octaborate tetrahydrate, which may also be used in the same concentration range as the sodium tetraborate decahydrate. Examples of other mold inhibitors that may be used include voriconazole, thiabendazole, thujaplicin, N-hydroxynaphtalimide, sodium acetate, sodium benzoate, calcium propionate, potassium sorbate, sodium formate, sodium nitrite, miconazole, ibuprofen, triazole, sodium triazole, difluconazole, amphotericin B, nystatin, thiabendazole, itraconazole, and clotrimazole.

In creating the solution or concentrate, the steps include the following basic sequence: first, dissolving the sodium carbonate in water in order to provide the proper pH for the solution, then adding the borate compound, preferably sodium tetraborate decahydrate, then the alkali metal silicate, preferably sodium metasilicate nonahydrate, and then optionally adding the mold inhibitor, preferably either the ethanolamine or the thymol. The solution is then stirred for some time period, preferably at least one hour. The product may also be made as a powder, in which the dry chemicals are mixed together, and can be added to a volume of water in order to create the solution for treatment. In such a case, the powder mixture may be prepared and shipped to a wood treatment facility, where the solution may be prepared on-site.

The preferred wood treatment includes placing the wood products into a vacuum tank or chamber, creating a vacuum (or low pressure, preferably below 2 inches of mercury), and allowing the wood products to remain in the vacuum or low pressure state for some certain time period, preferably about 45 minutes. Then, the wood products are immersed in the treatment solution, and then may optionally be brought up to an increased pressure of up to 50 inches of mercury to soak for a certain time period, preferably for 3 hours. The wood products are then removed from the solution and placed into a drying chamber or kiln having a temperature preferably in the range of 55 to 65° C. for some time period, preferably between 24 and 72 hours. Finally, the wood products are removed from the drying chamber or kiln, and allowed to cool down to room temperature.

The following example is used for illustrative purposes, and illustrates one embodiment of the proposed invention:

Example

Six samples of southern pine were selected by taking a piece of wood, and cutting it into six samples with the approximate dimensions of 2 cm×2 cm×6 cm. Sample sizes were small to accommodate the small size of the vacuum chamber. Each of the samples was dried in an oven at 60° C. for at least 24 hours before the treatment began, to ensure that each sample was dry.

A solution was prepared by dissolving 19.9 grams of sodium carbonate, 30.8 grams of sodium tetraborate decahydrate, 42.0 grams of sodium metasilicate nonahydrate, and 45.0 milliliters of ethanolamine in a solution with a volume of 900 milliliters. The solution was allowed to stir for one hour, before a homogeneous solution was achieved.

The samples were treated by placing them in a vacuum flask, which was then brought to a pressure of 1.6 inches of mercury, or 5.418 kPa. The wood samples were exposed to the vacuum for a minimum of 45 minutes. Following this, the samples were exposed to the sample solution. The samples were immersed in the solution at 31 inches of mercury, or 105 kPa for three hours. The samples were massed before and after treatment to determine retention of preservative.

The samples were then placed in another drying oven at 60° C., to accelerate drying. Once the samples achieved constant mass (24 hours), they were removed from the oven and were cooled to room temperature.

Flame Test:

Two untreated samples (UT 1-2) of the same size as the treated samples were held over a Bunsen burner flame for thirty seconds. The loss of mass for these samples is shown in Table 1. The treated samples (A-F) were also held over the flame for 30 seconds. The loss of mass for these samples is also reported in Table 1.

TABLE 1

| Sample | Percent mass lost | First sign of wood burning |
|---|---|---|
| UT 1 | 42% | 5 seconds |
| UT 2 | 45% | 11 seconds |
| A | 10% | Never |
| B | 8% | Never |
| C | 9% | 22 seconds |
| D | 11% | Never |
| E | 6% | Never |
| F | 8% | Never |

The samples treated with the borate/silicate mixture clearly show a resistance to flammability, at a silicate mass percentage of 1.5%.

One advantage to the aqueous wood treatment solution proposed herein is that the solution may be substituted into most standard wood pressure treatment techniques and processes that are currently employed in the pressure treatment industry. Typically, such treatment methods include the steps of placing the wood product into a pressure vessel and applying a vacuum, contacting the material with an aqueous solution and increasing the pressure in the pressure vessel, draining the aqueous solution and reducing the pressure, and drying the treated wood product. It should be understood that other treatments may be used, particularly a treatment wherein wood or wood products are subjected to a vacuum, and are then immersed in the proposed aqueous solution without applying further pressure, and are then dried. Various combinations of wood treatment steps may be used.

This proposed solution may be used in conjunction with any type of wood or wood products, including green lumber, timber, OSB, plywood, and other cellulosic products such as paper, felt paper and corrugated cardboard. For treatment of such other cellulosic products, pressure treatment may be unnecessary, as a dipping process followed by a drying process may be sufficient to impart the desired characteristics to the final product.

Although the present invention has been described in considerable detail with reference to certain preferred versions thereof, other versions are possible. Therefore, the spirit and scope of the appended claims should not be limited to the description of the preferred versions contained herein. All features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. An aqueous solution for the preservation of wood and wood products, said aqueous solution comprising:
   an alkali metal silicate comprising between about 5% and about 30% by mass of said solution a soluble borate comprising between about 1.5% and about 9% by mass of said solution; and an alkali metal carbonate comprising between about 1% and about 10% by mass of said solution.

2. The aqueous solution set forth in claim 1, wherein said alkali metal silicate is selected from the group consisting of sodium metasilicate nonahydrate, sodium orthosilicate, and potassium metasilicate.

3. The aqueous solution set forth in claim 1, wherein said soluble borate is selected from the group consisting of sodium tetraborate decahydrate and disodium octoborate tetrahydrate.

4. The aqueous solution set forth in claim 1, wherein said alkali metal carbonate is sodium carbonate.

5. The aqueous solution set forth in claim 1, further including a mold and mildew inhibitor.

6. The aqueous solution set forth in claim 5, wherein said mold and mildew inhibitor is ethanolamine.

7. The aqueous solution set forth in claim 6, wherein said ethanolamine comprises between about 0.5% to 20% by mass of said solution.

8. The aqueous solution set forth in claim 5, wherein said mold and mildew inhibitor is thymol.

9. The aqueous solution set forth in claim 8, wherein thymol comprises between about 0.01% to about 0.1% by mass of the solution.

10. The aqueous solution set forth in claim 5, wherein said mold and mildew inhibitor is selected from the group consisting of: voriconazole, thiabendazole, thujaplicin, N-hydroxynaphtalimide, sodium acetate, sodium benzoate, calcium propionate, potassium sorbate, sodium formate, sodium nitrite, miconazole, ibuprofen, triazole, sodium triazole, difluconazole, amphotericin B, nystatin, thiabendazole, itraconazole, and clotrimazole.

11. A treated wood product comprising
a wood product impregnated with a solution comprising an alkali metal silicate comprising between about 5% and about 30% by mass of said solution
a soluble borate comprising between about 1.5% and about 9% by mass of said solution; and
an alkali metal carbonate comprising between about 1% and about 10% by mass of said solution;
wherein said solution imparts to said wood product increased resistance to termites and other insects, increased resistance to fire, and increased resistance to water rot.

12. The treated wood product set forth in claim 11, wherein said alkali metal silicate is selected from the group consisting of sodium metasilicate nonahydrate, sodium orthosilicate, and potassium metasilicate.

13. The treated wood product set forth in claim 11, wherein said soluble borate is selected from the group consisting of sodium tetraborate decahydrate and disodium octoborate tetrahydrate.

14. The treated wood product set forth in claim 11, wherein said alkali metal carbonate is sodium carbonate.

15. The treated wood product set forth in claim 11, wherein said solution further includes a mold and mildew inhibitor.

16. The treated wood product set forth in claim 15, wherein said mold and mildew inhibitor is ethanolamine.

17. The treated wood product set forth in claim 16, wherein said ethanolamine comprises between about 0.5% to 20% by mass of said solution.

18. The treated wood product set forth in claim 15, wherein said mold and mildew inhibitor is thymol.

19. The treated wood product set forth in claim 18, wherein said thymol comprises between about 0.01% to about 0.1% by mass of said solution.

20. An aqueous solution comprising:
sodium metasilicate nonahydrate comprising between about 5% and about 30% by mass of said solution;
sodium tetraborate decahydrate comprising between about 1.5% and about 9% by mass of said solution; and
sodium carbonate to maintain pH of said solution within the range of about 9.5 to 13.

21. The aqueous solution set forth in claim 20, further comprising a mold inhibitor selected from the group consisting of ethanolamine and thymol.

22. A powder mixture that forms an aqueous solution when added to water, said powder mixture comprising:
A soluble alkali metal silicate in powder form
a soluble borate in powder form; and
a pH buffer in powder form;
wherein concentrations of said powder mixture after said water is added to said powder mixture to form a solution are such that the soluble alkali metal silicate comprises between about 5% and about 30% by mass of said solution, said soluble borate comprises between about 1.5% and about 9% by mass of said solution, and said pH buffer comprises between about 1% and about 10% by mass of said solution.

23. The powder mixture set forth in claim 22, wherein said alkali metal silicate is selected from the group consisting of sodium metasilicate nonahydrate, sodium orthosilicate, and potassium metasilicate.

24. The powder mixture set forth in claim 22, wherein said soluble borate is selected from the group consisting of sodium tetraborate decahydrate and disodium octoborate tetrahydrate.

25. The powder mixture set forth in claim 22, wherein said pH buffer is sodium carbonate.

26. The powder mixture set forth in claim 22, further including a mold and mildew inhibitor in powder form.

27. The powder mixture set forth in claim 26, wherein said mold and mildew inhibitor is selected from the group consisting of ethanolamine, thymol, voriconazole, thiabendazole, thujaplicin, N-hydroxynaphtalimide, sodium acetate, sodium benzoate, calcium propionate, potassium sorbate, sodium formate, sodium nitrite, miconazole, ibuprofen, triazole, sodium triazole, difluconazole, amphotericin B, nystatin, thiabendazole, itraconazole, and clotrimazole.

* * * * *